(12) United States Patent
Gabrielson et al.

(10) Patent No.: US 8,090,065 B2
(45) Date of Patent: Jan. 3, 2012

(54) IMPLIED CLOCK

(75) Inventors: Donn E. Gabrielson, Everett, WA (US);
Brent Chauvin, Snohomish, WA (US);
Blake W. Little, Bothell, WA (US)

(73) Assignee: SonoSite, Inc., Bothell, WA (US)

( * ) Notice: Subject to any disclaimer, the term of this patent is extended or adjusted under 35 U.S.C. 154(b) by 1735 days.

(21) Appl. No.: 11/289,761

(22) Filed: Nov. 29, 2005

(65) Prior Publication Data

US 2007/0121769 A1    May 31, 2007

(51) Int. Cl.
*H04L 7/00* (2006.01)
(52) U.S. Cl. ......... 375/356; 375/355; 375/362; 375/358
(58) Field of Classification Search .................. 375/354, 375/358, 359, 362; 455/458
See application file for complete search history.

(56) References Cited

U.S. PATENT DOCUMENTS

| | | | |
|---|---|---|---|
| 4,647,935 A | 3/1987 | Helbling | |
| 4,974,211 A | 11/1990 | Corl | |
| 5,587,709 A * | 12/1996 | Jeong | 341/100 |
| 5,673,295 A | 9/1997 | Read et al. | |
| 5,722,412 A * | 3/1998 | Pflugrath et al. | 600/459 |
| 5,778,214 A | 7/1998 | Taya et al. | |
| 5,782,769 A | 7/1998 | Hwang et al. | |
| 5,838,749 A | 11/1998 | Casper et al. | |
| 5,870,441 A | 2/1999 | Cotton et al. | |
| 5,930,722 A | 7/1999 | Han et al. | |
| 6,026,350 A | 2/2000 | Tustin et al. | |
| 6,104,279 A * | 8/2000 | Maletsky | 340/10.41 |
| 6,459,393 B1 | 10/2002 | Nordman | |
| 6,471,651 B1 * | 10/2002 | Hwang et al. | 600/459 |
| 6,553,505 B1 | 4/2003 | Brown et al. | |
| 6,665,754 B2 | 12/2003 | Mann | |
| 6,748,565 B1 | 6/2004 | Holmes et al. | |
| 6,812,750 B1 * | 11/2004 | Henrion et al. | 327/115 |
| 2002/0122514 A1 * | 9/2002 | Hofmann et al. | 375/354 |
| 2003/0214335 A1 * | 11/2003 | Saeki | 327/165 |
| 2005/0091559 A1 * | 4/2005 | Vining | 714/700 |
| 2006/0188046 A1 * | 8/2006 | Jain | 375/355 |
| 2007/0002941 A1 * | 1/2007 | Low et al. | 375/229 |

FOREIGN PATENT DOCUMENTS

| | | |
|---|---|---|
| EP | 0738057 A2 | 10/1996 |
| EP | 1355465 | 10/2003 |
| WO | WO 00/66001 A1 | 11/2000 |

OTHER PUBLICATIONS

Extended European Search Report issued for EP 06255916.6 dated Feb. 15, 2007.

* cited by examiner

*Primary Examiner* — Khanh C Tran
*Assistant Examiner* — Qutbuddin Ghulamali
(74) *Attorney, Agent, or Firm* — Perkins Coie LLP

(57) ABSTRACT

Systems and methods providing clocking between various components or sub-components are shown. Embodiments implement an implied clock technique which reduces the number of signal lines, signaling overhead required for an encoded clock signal, and/or and power consumption for a high speed communication link. In accordance with embodiments efficient communication is provided between a core device and a remote device by the core device providing both clock and data signals to the remote device and the remote device providing a data signal at a predetermined clock rate without communicating its clock signal. The core device of this embodiment determines an "implied clock" suitable for accurately receiving data from the remote device.

27 Claims, 4 Drawing Sheets

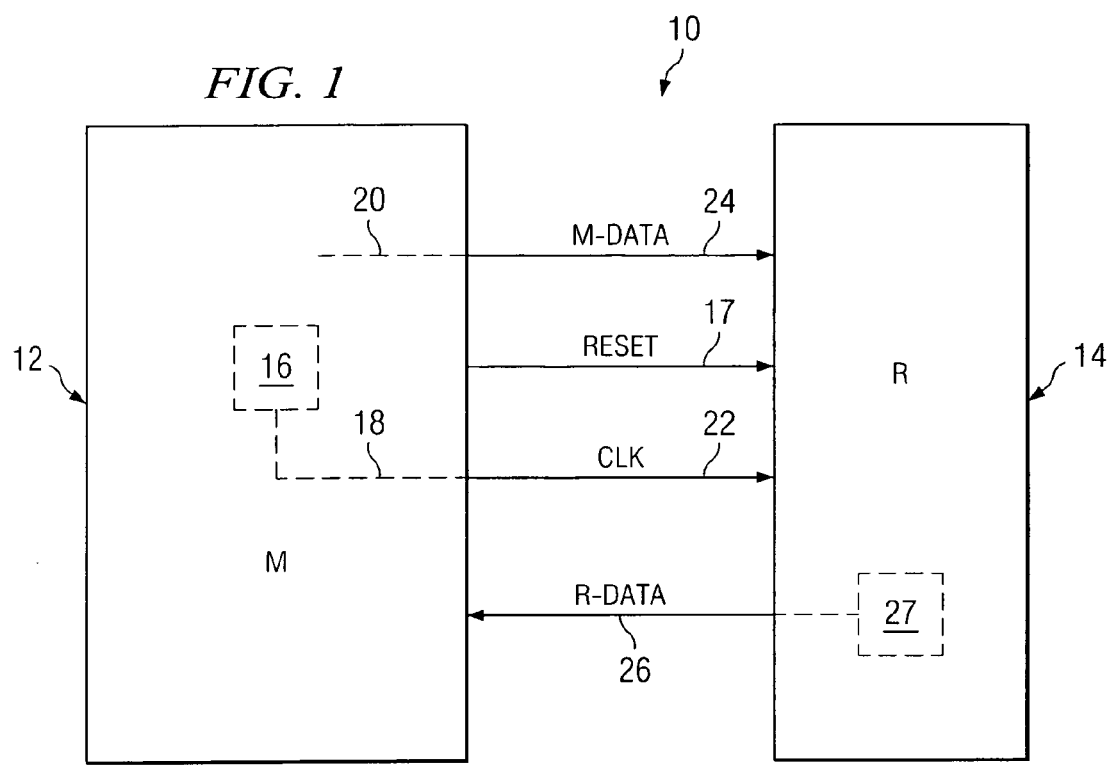
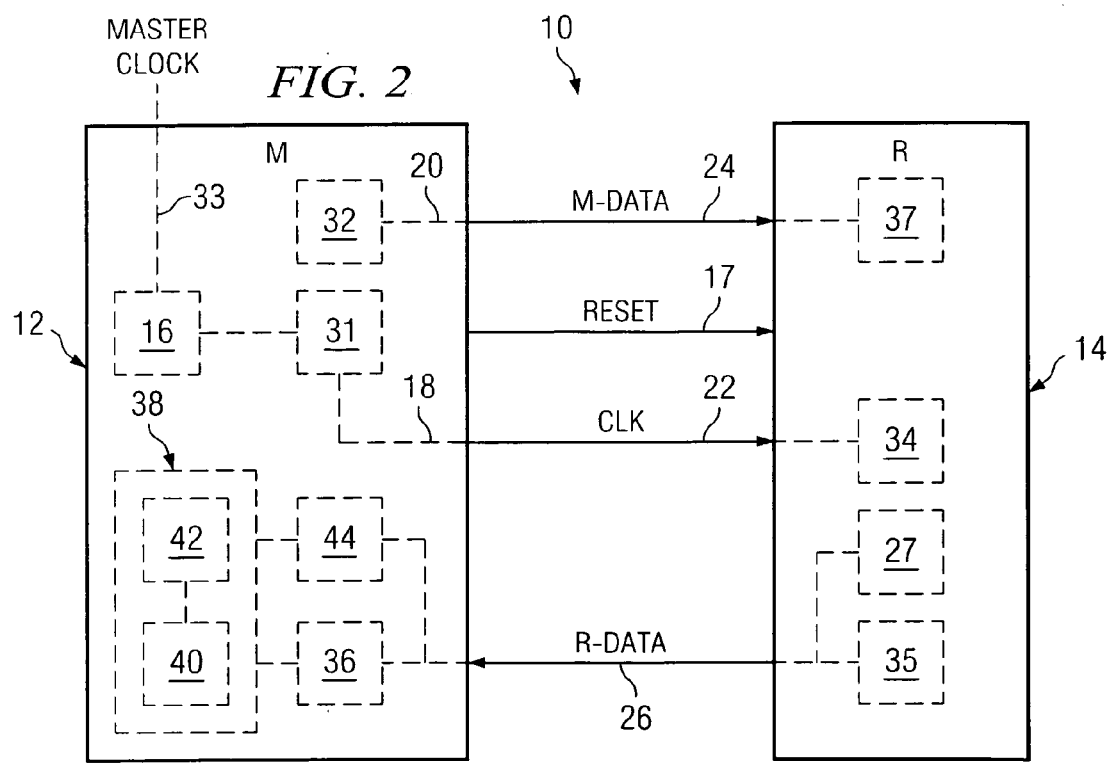

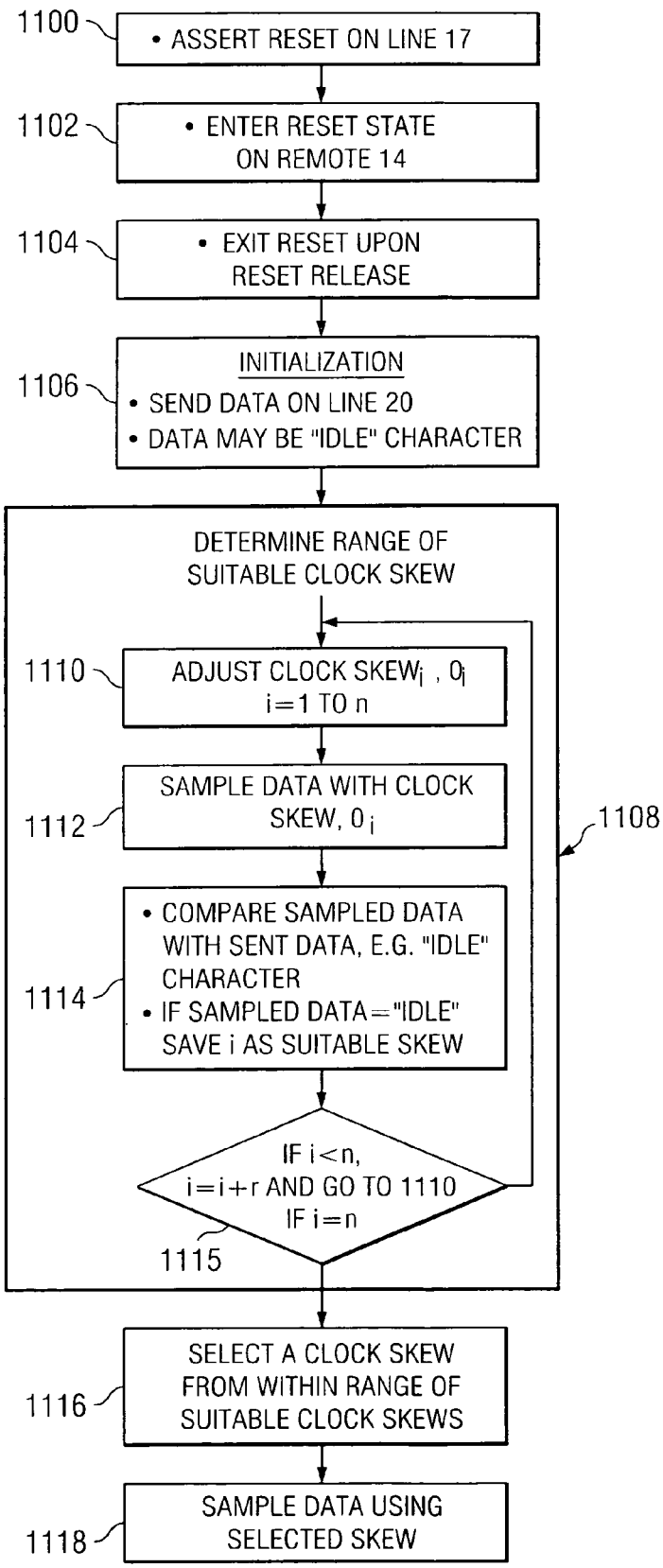

IMPLIED CLOCK

BACKGROUND OF THE INVENTION

The present invention relates to data communication and more particularly to high speed communication links.

As is well known, data transport between devices may include separated data and clock streams or a clock stream may even be encoded in the data stream. Each approach includes significant limitations. For example, having separate clock and data lines requires additional power, space and logic to support the communication link. Additionally, stable high speed communication on separate clock and data lines requires that the lines be accurately matched in length, size, etc. The use of separate clock and data paths will continue to be limited as processing speed continues to increase.

The issue of separate delay paths is eliminated when the clock signal is encoded within the data signal. However, an encoded signal may significantly increase the required transfer speed necessary to maintain device performance. For a given signaling speed the information transfer rate of a data signal encoded with a clock signal is lower than the data transfer rate would be along a separated data line. Similarly, at a fixed data transfer rate a data signal encoded with a clock signal would require faster processing speed as compare to a separated data line. Simply increasing the signaling speed may not be a viable option as faster processing may increase in power consumption, expense, etc.

With the ever increasing density of digital electronics, it would desirable to be able to reduce the number of signal lines while avoiding the limitations of encoded data streams.

BRIEF SUMMARY OF THE INVENTION

The present invention addresses the need for reducing the number of data lines and power consumption for a high speed communication link. Such communication links may be provided as traces upon a single board or device or as cables, etc. for a remotely located site or component. Aspects of the invention may be utilized in a variety of different applications. For example, serial or parallel communication between a processor and memory, a sensor unit and a data collection device or controller and processor to processor communication.

In accordance with the principles of the present invention, a system is provided which may exhibit a reduction in power required to support a communication link, improved ease of routing the communication link by eliminating the requirement of matched clock/data lines, a reduction in the number conductor count, and overall simplification of the processing of signals.

A system utilizing one embodiment of the invention may provide efficient communication between a core device and a remote device. The core device may provide both clock and data signals to the remote device. The clock and data signals may be provided on separate lines or, in another embodiment, the clock signal may be encoded with the data signal. However, rather than returning separate clock and data signals to the core device, the remote device may provide a data signal at a predetermined clock rate without communicating its clock signal. In turn, the core device may determine an "implied clock" suitable for accurately receiving data from the remote device. In an embodiment of the invention, the core device determines a clock rate at which data from the remote device is being transmitted in order to accurately and reliably utilize the data without the need for a separate clock signal line or encoded clock from the remote device. While the clock rate of the remote device can be predetermined, the phase of the data from the remote device may be found during a link initialization sequence. The core device of a preferred embodiment determines an implied clock for sampling data on a data line based on the predetermined clock rate and the clock skew revealed during a link initialization sequence.

A method of communication between a core device and a remote device in a system utilizing aspects of the present invention may include the steps of: transmitting a predetermined bit pattern within a data stream from the remote device to the core device; determining a range of clock signal phases for sampling the data stream to yield the predetermined bit pattern; selecting a phase from within the range of clock signal phases; and sampling the data stream utilizing clock signal information and the selected phase to communicate data between the remote device and the core device.

The present invention may be particularly well suited for application in small, battery powered devices, such as medical monitors, sensors, etc. Principles of the present invention may be utilized, for example, in a portable diagnostic ultrasound instrument which exhibits many of the features of a premium ultrasound system in a hand held unit. A portable ultrasonic diagnostic instrument may include an array transducer, a beamformer for delaying and combining echo signals received by elements of the array transducer, signal processing and imaging circuitry for processing the echo signals, and a display for the processed echo signals. The portable ultrasonic diagnostic instrument may operate from battery power, and power control may be provided for limiting power consumption, for example, by a system disclosed in Assignee's U.S. Pat. No. 6,471,651, incorporated herein by reference. Power reduction is particularly important for such a battery-powered system. In such a system, principles of the invention may be utilized to provide efficient communication between, for example, a sensor device and a controller. Application of the present invention may also yield a reduction in the number of traces or cables of a device and a reduction in the overall device size as well as a reduction in the device power requirements.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1 is a block diagram illustrating the architecture of an implied clock serial communication system 10 according an embodiment of the present invention.

FIG. 2 is a block diagram illustrating the architecture of an implied clock serial communication system 10 according an embodiment of the present invention.

FIG. 3 illustrates a flow chart of an embodiment of a link initialization sequence of the invention.

DETAILED DESCRIPTION OF THE INVENTION

Figure 4:
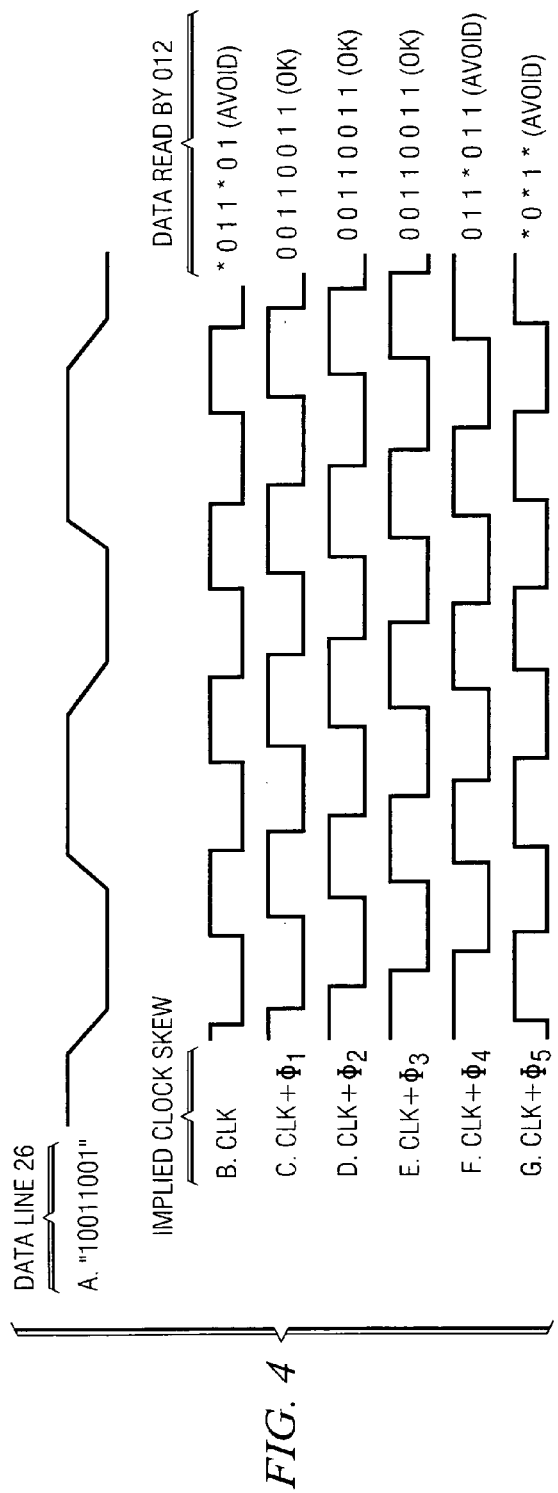
FIG. 4 illustrates aspects of link initialization according to an embodiment of the invention.

Referring first to FIGS. 1-2, architectures of embodiments of an implied clock serial communication system according to the present invention are illustrated in block diagram form. System 10 includes an embodiment of a main or core device 12 and a remote device 14. Core device 12 and remote device 14 may be in close proximity, for example, on the same circuit board or application specific integrated circuit (ASIC), or devices 12, 14 may be separated, even in geographically remote locations. Examples of a core device 12 and remote device 14 combination may include a processor and memory, a sensor unit and a data collection device or a processor to another processor.

Core device 12 of an embodiment includes a clock signal circuit 16 which is utilized, for example, in core processing and communication. Clock 16 may generate a clock signal internally (within core device 12) or utilize another clock input from another clock source, such as a master clock input 33 (FIG. 2). Core device 12 provides a clock signal 18 and data signal 20 which are communicated to remote device 14 via lines 22, 24, respectively. Lines 22, 24 may assume a variety of configurations depending on the particular application of system 10. For example, lines 22, 24 may be traces within an application specific integrated circuit (ASIC) or may be traces, wires, or cables routed between physically separated devices. In an ASIC application, for example, lines 22, 24 may utilize low voltage differential signaling wherein the clock signal is provided on a pair of wires and the data signal is provided on a different pair of wires. Each pair of wires is balanced electrically so when one of the wires is driven high the other wire is low, and vice versa. Data on lines 22, 24 may be provided at the system clock rate or multiples or divisions thereof. Additionally, the remote device 14 may multiply or divide the system clock and utilizing a higher clock speed as compared to the core device 10.

Data from remote device 14 is transmitted to core device 12 via data line 26. Remote device 14 includes a clock system 27 incorporating, for example, a phase lock loop capable of generating a clock signal(s) at multiples or divisions of the core device's clock system. For example, with a core device 12 operating at 100 megahertz, the clock of the remote device 14 may operate at 400 megahertz. In one embodiment, data line 26 may be a low voltage differential signal line. Remote device 14 need not communicate its clock signal to core device 12. Instead the core device 12 determines an "implied clock" suitable for accurately receiving data from remote device 14. In an embodiment of a system having multiple remote devices 14, information from each remote device 14 may be received on a separate data line and the core device 12 may reconstruct the data from each remote device 14 by determining an implied clock for each remote device 14.

Core device 12 determines a clock rate at which data from remote device 14 is being transmitted in order to accurately and reliably utilize the data without the need for a separate clock signal line or encoded clock from remote device 14 to core device 12. The clock rate can be a multiple or a division of the clock as configured on the core device 12. While clock rate of the remote device 14 can be predetermined, the phase of the data from remote device 14 is found during a link initialization sequence of an embodiment of the present invention. In other words, while the clock rate is known, clock skew is determined by the core device 12 of embodiments of the invention in order to accurately receive data from remote device 14. As will be further described, core device 12 of a preferred embodiment determines an implied clock for sampling data on data line 26 based on the predetermined clock rate and the clock skew revealed during the link initialization sequence.

FIG. 2 illustrates aspects of an embodiment of the invention wherein a serial communication system 10 includes a core device 12 and remote device 14. Core device 12 includes a clock signal circuit 16 and a transmitter 31 used as a means for transmitting a clock signal 18 from the core device 12 to the remote device 14. Transmitter 32 is used to transmit data 20 from core device 12 to remote device 14. In another embodiment the clock signal 18 may be encoded with the data signal transmitted to the remote device 14. Clock signal unit 16 may generate a clock internally or utilize an external clock, such as a master clock signal received at input 33 from a common clock source. By using a common clock source, extra clock line(s) and routing issues (matching, etc.) may be avoided. Remote device 14 includes a receiver 37 used to receive data 20 on line 24 from core device 12 and a transmitter 35 for transmitting data to the core device 12 along line 26. Remote device 14 of the illustrated embodiment further includes a receiver 34 for receiving the clock signal from the core device 12. Core device 12 includes a receiver 36 for receiving the data from the remote device 14 along line 26. Core device 12 further includes a link initializer circuit 38 having a phase range determination circuit 40. Phase range determination circuit 40 determines a range of clock signal phases for sampling the data on line 26. Phase selection circuit 42 selects a phase from within a range of suitable clock signal phases. Core device 12 also includes a data sampler 44 using the clock signal and selected phase information from phase selection circuit 42 to sample the data stream on line 26 to communicate data from remote device 14 to core device 12.

Embodiments of the invention may be implemented in hardware, software or combinations thereof. For example, aspects of the system 10 may be implemented on a controller with software.

One particular link initialization sequence, used for example in the link initializer circuit 38 of FIG. 2, will now be described with reference to FIG. 3. At a first step 1100, core device 12 asserts a Reset on data line 17 which prompts remote device 14 to enter a Reset state 1102. After the Reset is released 1104, core device 12 waits for data transitions on data line 26. During an initialization procedure 1106, remote device 14 sends a predetermined data set on data line 26. The data set may include a repeated 4 bit pattern, such as "1001" or "1100." Such a pattern can be characterized as an "idle character." Bit patterns of different size or value may also be practicable as idle characters. Preferably the idle character is uniquely identifiable. At this point 1106, a data stream on data line 26 includes repeated idle characters provided at a known clock rate (e.g., a multiple or division of the core device 12 clock rate), but with an undetermined clock skew. Depending on the clock skew value, data sample on data line 26 may or may not be recognized as idle characters. Proper clock skew is used to accurately sample the data on line 26. In other words, while core device 12 receives repeated idle characters, core device 12 can accurately recognize the idle characters as such only by sampling data line 26 at a known clock rate and with a suitable clock skew. Embodiments of the invention may provide a real-time approach to tracking the phase shift of the link. A phase tracking algorithm could be active at certain intervals when the link is idle (with idle characters passing from remote device 14 to core device 12) in order to track the phase and make minor adjustments to the phase of the data receiver(s). Such real-time tracking may allow for compensation of phase shift drifting due to changing temperatures, voltages, etc. One approach that may be used is to provide a "predictable" or defined message size that allows the system to determine whether the link is active or idle. In embodiments with the idle character within the message body, the system could determine when the link transitions to carrying idle characters by having message size information.

Core device 12 of an embodiment of the invention determines a preferred clock skew by first determining a range of clock skews providing accurate data communication at step 1108. As described herein, core device 12 determines the range of clock skew by adjusting the clock skew at step 1110, sampling the data at the clock skew at step 1112, comparing the sampled data to the idle character 1114 (if sampled data equals "idle" character, save as a suitable skew), and selectively repeating the process of step 1108 with iterative adjustments to the clock skew at step 1115. Once a range of suitable clock skews has been determined, a particularly desired or optimum clock skew may be selected at step 1116. For example, the median clock skew of the range of suitable clock skews of can be used. Alternatively, an average or filtered average of the clock skews could be used. Once a preferred clock skew has been determined, core device 12 can receive data from remote device 14 without a clock signal from remote device 14 at step 1118 by sampling at the predetermined clock rate with the preferred clock skew.

FIG. 4 illustrates aspects of a link initialization concept using, for example, the architecture of FIG. 1. Line A represents data provided on data line 26 by remote device 14 and includes repeated idle characters of "1001." Lines B-G of FIG. 4 represent clock signals with increasing clock skews and the "Data Read" column represents data sampled by core device 12 at a clock rate with an associated skew. Line B represents a clock signal with no skew and data sampled may include numerous indeterminate values as sampling occurs near transitions of the data on data line 26. As a result, a clock skew of $\phi$ should be avoided. Line C represents a clock rate with a skew of $\phi_1$. Sampling at this skew results in an accurate capture of the idle characters, as the "1001" pattern is read by core device 12. Similarly, lines D-E represent greater clock skews $\phi_2$-$\phi_3$ with data sampling accurately capturing the idle characters. Line F represents a still greater clock skew $\phi_4$ with data sampling potentially unable to accurately capture the idle characters. Similarly, Line G represents a greater clock skew $\phi_5$ with potentially inaccurate capture of the idle characters.

In the example of FIG. 4, a range of suitable clock skews can be defined. Data sampling within the range of clock skews of $\phi_1$-$\phi_3$ results in accurate capture of the idle character, and therefore accurate capture of subsequent non-idle character data. A particularly desired clock skew may be the median clock skew of $\phi_2$. Once a preferred clock skew has been determined, core device 12 can receive data from remote device 14 without a clock signal from remote device 14. FIG. 4 illustrates the broad concept of selecting an optimum clock skew for sampling data on data line 26. In other embodiments, the division of clock skews can be greater in order to determine a more accurate, preferred clock skew for sampling.

Figure 5:
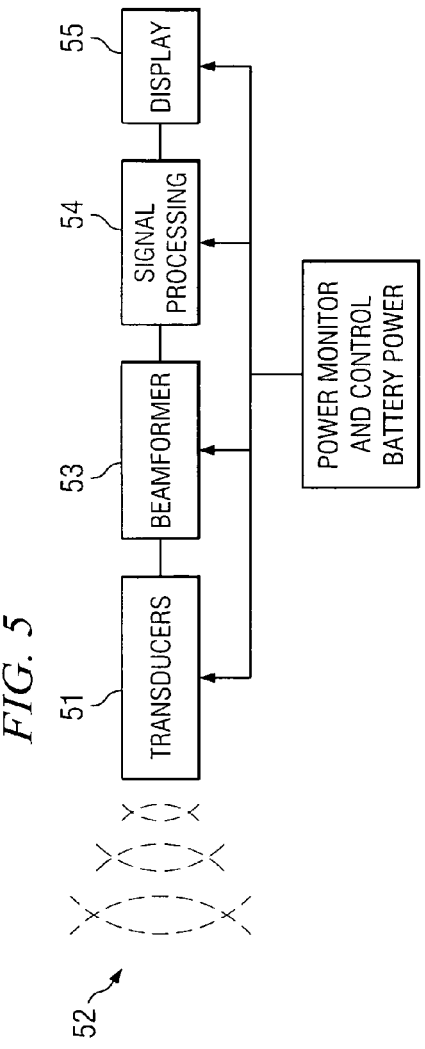
FIG. 5 illustrates architecture of a portable ultrasonic diagnostic instrument adapted according to an embodiment of the present invention.

FIG. 5 illustrates architecture of a portable ultrasonic diagnostic instrument, such as disclosed in U.S. Pat. No. 6,471,651, incorporated herein by reference, adapted to implement an embodiment of the invention. Ultrasound transducers 51 generate ultrasonic waves shown generally at 52 and receive reflections of the ultrasonic waves. Wave generation and echo signal processing is accomplished by a beamformer circuit 53 which interfaces with the transducers 51. Signals from beamformer 53 are then passed to a signal processor 54, and the process signals are then used to control a display 55. Beamforming circuit 53 and signal processor 54 may be separate ASIC devices.

Figure 6:
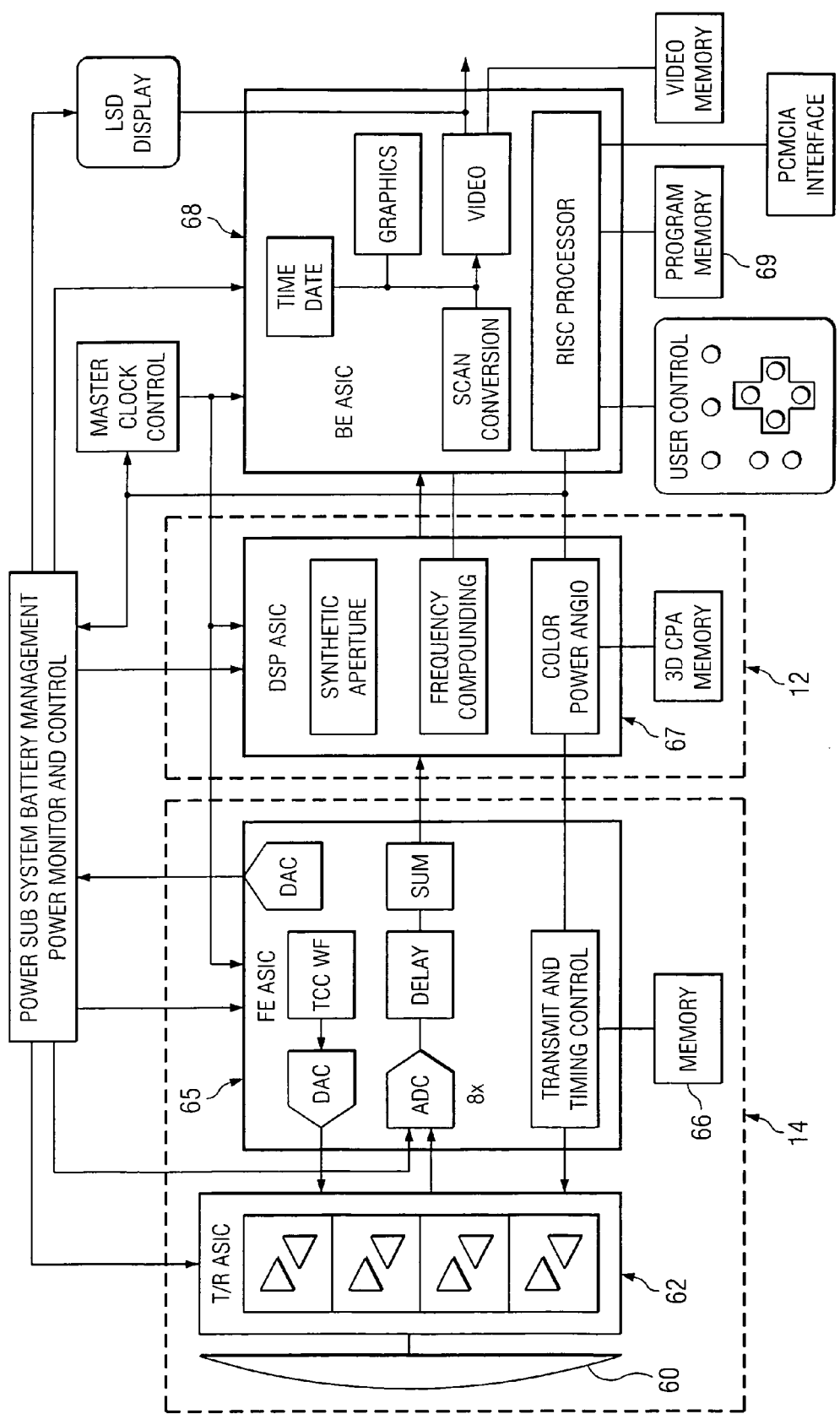
FIG. 6 is a more detailed functional block diagram of the ultrasonic diagnostic instrument of FIG. 5.

FIG. 6 is a more detailed functional block diagram of an ultrasonic diagnostic instrument. The instrument is described in more detail in U.S. Pat. No. 5,722,412, which is incorporated herein by reference. In this instrument a transducer array 60 is used for its solid state, electronic control capabilities, variable aperture, image performance and reliability. The elements of the array are connected to a transmit/receive ASIC 62 which drives the transducer elements and receives echoes received by the elements. ASIC 62 may be defined by four separate ASICs. The transmit/receive ASIC 62 also controls the transmit and receive apertures of the array and the gain of the received echo signals. Echoes received by the transmit/receive ASIC 62 are provided to the adjacent front end ASIC 65, which beamforms the echoes from the individual transducer elements into scanline signals. The front end ASIC 65 also controls the transmit waveform, timing, aperture and focusing. In the illustrated embodiment the front end ASIC 65 provides timing signals for the other ASICs, time gain control, and monitors and controls the power applied to the transducer array, thereby controlling the acoustic energy which is applied to the patient and minimizing power consumption of the unit. A memory device 66 is connected to the front end ASIC 65, which stores data used by the beamformer. Beamformer scanline signals are coupled from the front end ASIC 65 to the adjacent digital signal processing ASIC 67. The digital signal processing ASIC 67 filters the scanline signals and in the preferred embodiment may also provides several advanced features including synthetic aperture formation, frequency compounding. Doppler processing such as power Doppler (color power angio) processing, and speckle reduction. The ultrasound B mode and Doppler information is then coupled to the adjacent back end ASIC 68 for scan conversion and the production of video output signals. A graphics processor overlays the ultrasound image with information such as depth and focus markers and cursors. Frames of ultrasonic images are stored in a video memory coupled to the back end ASIC 68. The back end ASIC 68 also includes the central processor for the ultrasound system, a RISC (reduced instruction set controller) processor. The RISC processor is coupled to the front end and digital signal processing ASICs to control and synchronize the processing and control functions throughout the hand-held unit. A program memory 69 is coupled to the back end ASIC 68 to store program data which is used by the RISC processor to operate and control the unit.

The transmit/receive ASIC 62 includes four ASICs. These ASICs, along with ASIC 65, Memory 66 and Transducer Array 60 may be considered a "remote device" relative to FE ASIC 67, which may be considered the "core device." FE ASIC 67 may work in concert with one or more FPGAs having digital clock modules—or "DCMs." In this example, four DCMs are utilized with a DCM allocated to each remote channel. The DCM allows changes to both clock frequency and the clock phase. Each DCM is utilized in a serial link initialization sequence as described above wherein clock skew is adjusted, data is sampled and compared to an idle character, and a range of suitable clock phases for subsequent data sampling is determined. The FPGA can subsequently reprogram the DCM to have a phase shift within the middle of the phase shift range that accurately captured the idle characters. Subsequent data communication can occur on the data lines without clocks (other than the clock internal to the FPGA). The FPGA may be programmed to monitor a data stream and process data upon receipt of non-idle characters representing the start of a message from the remote site. The remote site may return to sending a data stream of idle characters upon end of message. The FPGA subsequently recognizes the idle characters as relating to the end of the message.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of serial communication between a core device and a remote device comprising the steps of:
    transmitting a core clock signal from the core device to the remote device;
    deriving a remote clock signal by the remote device from said core clock signal wherein said remote clock signal is at a known rate that is a multiple or division of said core clock signal and said remote clock signal is not communicated to the core device;
    transmitting a predetermined bit pattern within a data stream from the remote device to the core device, said predetermined bit pattern being transmitted during idle times of a communication link between the core device and the remote device and wherein said data stream is transmitted at said known rate of said remote clock;
    determining a range of clock signal phases for sampling the data stream to yield the predetermined bit pattern;
    sampling the data stream using a plurality of clock signal phases of the range of clock signal phases to provide a corresponding resultant bit pattern;
    identifying two or more of the clock signal phases which yield the predetermined bit pattern;
    selecting a phase from the plurality of clock signal phases for which the resulting bit pattern was identified as yielding the predetermined bit pattern; and
    sampling the data stream utilizing the known clock rate of said remote clock and the selected phase to communicate data between the remote device and the core device.

2. The method of claim 1, wherein the step of determining includes the steps of selecting a clock phase, sampling the data stream from the remote device utilizing the selected clock phase, and comparing a sampled value to the predetermined bit pattern.

3. The method of claim 2, wherein the step of determining includes repeated steps of selecting different phases and sampling the data stream utilizing the different phases.

4. The method of claim 1, wherein the step of selecting a phase includes selecting an optimum value of the range of phases.

5. The method of claim 1, wherein the data stream includes repeated predetermined bit patterns during the step of determining a range of clock signal phases.

6. The method of claim 5, wherein the predetermined bit patterns are separate messages within the data stream having a defined or predictable message size.

7. The method of claim 1, further comprising the step of: transmitting a data signal and a clock signal from the core device to the remote device.

8. The method of claim 7, wherein the known clock rate is a multiple or division of a clock signal transmitted from the core device to the remote device.

9. The method of claim 7, wherein the data signal and the clock signal are transmitted to the remote device on separate data lines.

10. The method of claim 1, wherein the remote device includes a plurality of separate remote devices and the steps of transmitting, determining, selecting and sampling are performed in association with each of the plurality of separate remote devices.

11. The method of claim 1, wherein the core device includes a controller and the remote device includes a transducer unit of an ultrasound device.

12. The method of claim 11, wherein the ultrasound device is a handheld, battery powered device.

13. The method of claim 1, wherein the selected phase is an optimum clock skew for sampling data chosen from the plurality of clock signal phases using a predetermined algorithm.

14. A serial communication system comprising:
    means for transmitting a core clock signal from a core device;
    means for receiving the core clock signal at a remote device;
    means for generating a remote clock signal at said remote device, wherein said remote clock signal is at a known clock rate that is a multiple or division of said core clock signal;
    means for transmitting a predetermined data signal during times when a communication link between the core device and the remote device is idle, wherein the predetermined data signal is transmitted from the remote device to the core device at the known clock rate wherein said remote clock signal is not transmitted with said data signal;
    means for determining a range of clock signal phases for sampling the data stream to yield the predetermined data signal;
    means for sampling the data stream using a plurality of clock signal phases of the range of clock signal phases to provide a corresponding resultant bit pattern;
    means for identifying two or more of the resultant bit patterns which yield the predetermined bit pattern;
    means for selecting a phase from the plurality of clock signal phases for which the resulting bit pattern was identified as yielding the predetermined bit pattern; and means for sampling the data stream using the known clock rate and the selected phase.

15. The system of claim 14, wherein the means for determining a range of clock signal phases includes means for selecting a clock phase, means for sampling the data stream from the remote device utilizing a selected clock phase, and means for comparing a sampled value to the predetermined bit pattern.

16. The system of claim 15, wherein the means for determining the range includes means for repeatedly selecting different phases and means for repeatedly sampling the data stream utilizing the different phases.

17. The system of claim 14, wherein the means for selecting a phase selects an optimum value of the range of phases.

18. The system of claim 14, wherein the means for selecting a phase includes means for selecting an optimum clock skew for sampling data chosen from the plurality of clock signal phases using a predetermined algorithm.

19. A signal processor for an ultrasonic device comprising:
an ultrasonic transducer having a clock signal receiving circuit for receiving a clock signal from a controller and creating a remote clock signal at a known clock rate that is a multiple or division of the received clock signal, and a transmitter for sending a predetermined data signal during idle times of a communication link between the ultrasonic transducer and the controller, wherein the predetermined data signal is transmitted at said known clock rate to the controller without sending said remote clock signal;
a link initializer circuit which determines a range of clock phases for sampling the data stream to yield the predetermined data signal;
a phase selection circuit which selects a preferred clock phase from within the range of clock phases; and
a data sampler using the known clock rate and the preferred clock phase to sample the data stream to communicate data from the ultrasonic transducer to the controller;
wherein the link initializer circuit samples the data stream using a plurality of clock signal phases of the range of clock signal phases to provide a corresponding resultant bit pattern, identifies two or more of the resultant bit patterns which yield the predetermined bit pattern, and said phase selection circuit determines said preferred clock signal phase by selecting a clock signal phase from the plurality of clock signal phases for which the resultant bit pattern was identified as yielding the predetermined bit pattern.

20. The signal processor of claim 19, wherein the ultrasonic transducer and controller are associated with a handheld, battery powered device.

21. The signal processor of claim 19, wherein the link initializer circuit selects a clock phase, samples the data stream from the transducer utilizing the selected clock phase, and compares a sampled value to the predetermined bit pattern.

22. The signal processor of claim 19, wherein the link initializer circuit repeatedly selects different phases and samples the data stream utilizing the different phases.

23. The signal processor of claim 19, wherein the phase selection circuit selects an optimum value of the range of clock signal phases.

24. The signal processor of claim 19, wherein the preferred clock signal phase is an optimum clock skew for sampling data chosen from the plurality of clock signal phases using a predetermined algorithm.

25. A serial communication system for an ultrasonic diagnostic device comprising:
means for transmitting a controller clock signal to an ultrasonic transducer;
means for receiving the controller clock signal at the ultrasonic transducer;
means for generating a remote clock signal at the ultrasonic transducer wherein said remote clock operates at a known clock rate and the known clock rate is a multiple or division of the controller clock rate;
means for transmitting a predetermined data signal during idle times on a communication link between the ultrasonic transducer and the controller, wherein the predetermined data signal is transmitted from the ultrasonic transducer to a controller at the known clock rate without transmitting said remote clock signal;
means for determining a plurality of clock signal phases for sampling the data stream from the ultrasonic device to which yield the predetermined data signal;
means for selecting a phase from the plurality of clock signal phases wherein the selected phase is an optimum clock skew for sampling data chosen from the plurality of clock signal phases using a predetermined algorithm; and
means for sampling the data stream from the ultrasonic transducer using the known clock rate and the selected phase.

26. The serial communication system of claim 25, wherein the means for determining a range of clock signal phases selects a clock phase, samples the data stream from the ultrasonic transducer utilizing a selected clock phase, and compares a sampled value to the predetermined bit pattern.

27. The serial communication system of claim 26, wherein the means for determining the range repeatedly selects different phases and repeatedly samples the data stream utilizing the different phases.

* * * * *